(12) United States Patent
Saito

(10) Patent No.: US 9,618,743 B2
(45) Date of Patent: Apr. 11, 2017

(54) ADAPTIVE OPTICS SYSTEM WITH POLARIZATION SENSITIVE SPATIAL LIGHT MODULATORS

(71) Applicant: CANON KABUSHIKI KAISHA, Tokyo (JP)

(72) Inventor: Kenichi Saito, Pittsford, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 14/670,140

(22) Filed: Mar. 26, 2015

(65) Prior Publication Data

US 2016/0278632 A1    Sep. 29, 2016

(51) Int. Cl.
| G02B 27/00 | (2006.01) |
| A61B 3/14 | (2006.01) |
| A61B 3/10 | (2006.01) |
| A61B 3/00 | (2006.01) |
| G02B 27/28 | (2006.01) |

(52) U.S. Cl.
CPC ........ *G02B 27/0068* (2013.01); *A61B 3/0025* (2013.01); *A61B 3/1015* (2013.01); *A61B 3/14* (2013.01); *G02B 27/283* (2013.01)

(58) Field of Classification Search
CPC ....... A61B 3/1025; A61B 3/14; A61B 3/1015; A61B 3/0025; A61B 3/13
See application file for complete search history.

(56) References Cited

U.S. PATENT DOCUMENTS

| 6,577,428 B2 | 6/2003 | Stappaerts |
| 7,458,687 B2 | 12/2008 | Silverstein et al. |
| 8,132,913 B2 | 3/2012 | Hirose et al. |
| 8,237,835 B1 | 8/2012 | Muller |
| 2011/0096293 A1* | 4/2011 | Hirose ............... A61B 3/102 351/206 |
| 2011/0096337 A1 | 4/2011 | Hirose et al. |
| 2013/0107360 A1 | 5/2013 | Kurtz et al. |
| 2013/0206963 A1 | 8/2013 | Grund |
| 2013/0234698 A1 | 9/2013 | Dorner |

(Continued)

FOREIGN PATENT DOCUMENTS

| EP | 2650661 A1 | 10/2013 |
| WO | 03/020121 A1 | 3/2003 |

(Continued)

OTHER PUBLICATIONS

Liquid Crystal Spatial Light Modulator, pp. 46-49, General Microtechnology & Photonics, Renens, CH, 2005 <URL: http://www.gmp.ch/htmlarea/pdf/SLMs.pdf>, retrieved on Mar. 19, 2014.

(Continued)

*Primary Examiner* — Darryl J Collins
*Assistant Examiner* — Journey Sumlar
(74) *Attorney, Agent, or Firm* — Canon U.S.A., Inc. IP Division

(57) ABSTRACT

An adaptive optical imaging system for imaging an object including a first polarization sensitive spatial light phase modulator and a second polarization sensitive spatial light phase modulator and a polarization adjustment device that converts the polarization of light that has passed through the first modulator before it irradiates the object and converts the polarization of the reflected light before it passes through the second modulator.

21 Claims, 7 Drawing Sheets

(56) References Cited

U.S. PATENT DOCUMENTS

| | | | |
|---|---|---|---|
| 2014/0071456 A1 | 3/2014 | Podoleanu et al. | |
| 2014/0160435 A1* | 6/2014 | Saito | A61B 3/14 351/221 |
| 2014/0176907 A1* | 6/2014 | Nozato | A61B 3/1015 351/206 |
| 2014/0293254 A1* | 10/2014 | Komatsuda | G03F 7/70108 355/67 |

FOREIGN PATENT DOCUMENTS

| | | |
|---|---|---|
| WO | 2014/027204 A1 | 2/2014 |
| WO | 2014/033483 A1 | 3/2014 |

OTHER PUBLICATIONS

Eun Jin Bae, Kyoung Rae Kim, Stephen H. Tsang, Sung Pyo Park, Stanley Chang, Retinal Damage in Chloroquine Maculopathy, Revealed by High Resolution Imaging: A Case Report Utilizing Adaptive Optics Scanning Laser Ophthalmoscopy, Korean Journal of Ophthalmology, Jan. 21, 2014, 28(1):100-107, The Korean Ophthalmological Society, Seoul, KR, 2014.

Futoshi Hirose, Koji Nozato, Ken-ichi Saito, Yasuyuki Numajiri, A Compact Adaptive Optics Scanning Laser Ophthalmoscope with High-Efficiency Wavefront Correction Using Dual Liquid Crystal on Silicon—Spatial Light Modulator, Proceedings of the SPIE, Ophthalmic Technologies XXI, Feb. 11, 2011, vol. 7885, Article 788515, pp. 1-7, SPIE, Bellingham WA, 2011.

Toco Y. P. Chui, Dean A. Vannasdale, Stephen A. Burns, The Use of Forward Scatter to Improve Retinal Vascular Imaging with an Adaptive Optics Scanning Laser Ophthalmoscope, Biomedical Optics Express, Sep. 13, 2012, 3(10):2537-2549, OSA, Washington DC, 2012.

Yan Zhang, Barry Cense, Jungtae Rha, Ravi S. Jonnal, Weihua Gao, Robert J. Zawadzki, John S. Werner, Steve Jones, Scot Olivier, Donald T. Miller, High-Speed Volumetric Imaging of Cone Photoreceptors with Adaptive Optics Spectral-Domain Optical Coherence Tomography, Optics Express, May 15, 2006, 14(10):4380-4394, OSA, Washington DC, 2006.

R. Daniel Ferguson, Zhangyi Zhong, Daniel X. Hammer, Mircea Mujat, Ankit H. Patel, Cong Deng, Weiyao Zou, Stephen A. Burns, Adaptive Optics Scanning Laser Ophthalmoscope with Integrated Wide-Field Retinal Imaging and Tracking, Journal of the Optical Society of America A, Oct. 18, 2010, 27(11):A265-A277, OSA, Washington DC, 2010 (NIH Public Access, Author Manuscript).

* cited by examiner

ADAPTIVE OPTICS SYSTEM WITH POLARIZATION SENSITIVE SPATIAL LIGHT MODULATORS

BACKGROUND

Field of Art

The present disclosure relates to a system and method for an adaptive optics system as used in scanning light ophthalmoscopes.

Description of the Related Art

In recent years, scanning light ophthalmoscopes (SLOs) that irradiate the fundus with laser light in two dimensions and receive reflected light therefrom and imaging apparatuses that utilize the interference of low coherence light have been developed as ophthalmic image pickup apparatuses. Thus, SLOs have become important tools for the study of the human retina in both normal and diseased eyes.

The resolution of such ophthalmic image pickup apparatuses has been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images.

One solution to this issue is an adaptive optics SLO (AO-SLO) in which the adaptive optics (AO) includes a correction optical system that measures the aberration of the eye and corrects the aberration. The AO-SLO or an adaptive optics optical coherence tomograph (AO-OCT) can measure the wavefront of the eye using a Shack-Hartmann wavefront sensor system. A deformable mirror or a spatial-phase modulator can then be driven to correct the measured wavefront, and an image of the fundus can then be acquired. This technique allows for the AO-SLO or the AO-OCT to obtain high resolution images of fundus despite the aberration introduced by intervening material such as the cornea and the lens of the eye.

SUMMARY

An adaptive optical imaging system for imaging an object. The adaptive optical imaging system receives irradiation light to irradiate the object. The adaptive optical imaging system includes a first modulator that is a polarization sensitive spatial light phase modulator, so as to modulate the irradiation light with a first polarization and does not substantially modulate light with a second polarization that is orthogonal to the first polarization. The adaptive optical imaging system includes a polarization adjustment device that converts the polarization of light that has passed through the first modulator before it irradiates the object and converts the polarization of the reflected light, such that the reflected light has a second polarization that is orthogonal to the first polarization. The adaptive optical imaging system includes a second modulator that is a polarization sensitive spatial light phase modulator, placed between a light source of the irradiation light and the polarization adjustment device so as to not modulate the irradiation light and modulate the reflected light. The adaptive optical imaging system includes a wavefront sensor that measures the wavefront of the reflected light. The adaptive optical imaging system includes an image signal detector. The adaptive optical imaging system includes a controller that sends first instructions to the first modulator to correct the aberration of the irradiation light on the object. The controller sends second instructions to the second modulator to correct the aberration of the reflected light on the image signal detector.

The adaptive optical imaging system may include the light source that produces the irradiation light. The adaptive optical imaging system may include a polarizer that turns irradiation light produced by the light source into polarized irradiation light. In the adaptive optical imaging system the polarized irradiation light may be linearly polarized irradiation light.

In the adaptive optical imaging system the polarization adjustment device may be a quarter wave plate.

In the adaptive optical imaging system the object being imaged may be an eye.

In the adaptive optical imaging system the first modulator may be a liquid crystal phase modulator.

In the adaptive optical imaging system the image signal detector may be a confocal imaging detector that includes a pinhole. The controller may send second instructions to the second modulator that focuses the reflected light as it enters the pinhole of the confocal imaging detector by correcting or altering the aberrations in the wavefront of light.

In the adaptive optical imaging system may include a polarization beam splitter. The polarization beam splitter may be arranged to receive the irradiation light from a first direction. The polarization beam splitter may be arranged to output the irradiation light with the first polarization in a second direction from the polarization beam splitter. The polarization beam splitter may be arranged to receive the reflected light with the second polarization that has been modulated by the second modulator from a third direction that is substantially parallel to the second but in the opposite direction. The polarization beam splitter may be arranged to output the reflected light with the second polarization that has been modulated by the second modulator in a fourth direction that is different from the first direction.

In the adaptive optical imaging system a tilt signal may be added to the second modulator such that a position at which the reflected light is focused on the detector is shifted.

The adaptive optical imaging system, wherein the image signal detector maybe a confocal imaging detector that includes a pinhole. The reflected which has been shifted by the tilt function maybe shifted relative to the pinhole.

The adaptive optical imaging system, wherein the first instructions that the controller may send to the first modulator take into account first calibration information which represents first distortions of a first wavefront that is used to irradiate the object. The first distortions may include distortions caused by optical components between the object and the light source of the irradiation light. The first distortions may also include distortions caused by the source of the irradiation light.

The adaptive optical imaging system, wherein the second instructions that the controller may send to the second modulator take into account second calibration information which represents second distortions of a second wavefront of reflected light that is incident on the image signal detector. The second distortions may include distortions caused by optical components between the object and the image signal detector. The second distortions may include distortions caused by optical components between the object and the wavefront sensor.

In the adaptive optical imaging system the first instructions may be used to adjust the shape of the irradiation light on the object.

The adaptive optical imaging system, wherein the first instructions may be used to adjust the shape of the reflected light on the image signal detector.

In the adaptive optical imaging system the object being imaged may be a fundus of an eye.

In the adaptive optical imaging system the irradiation light and the reflected light may both pass through the first modulator, the second modulator, and the polarization adjustment device.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following can be applied to an object to be inspected such as an eye to be inspected, skin, and internal organs.

AO-SLO

Figure 1A:
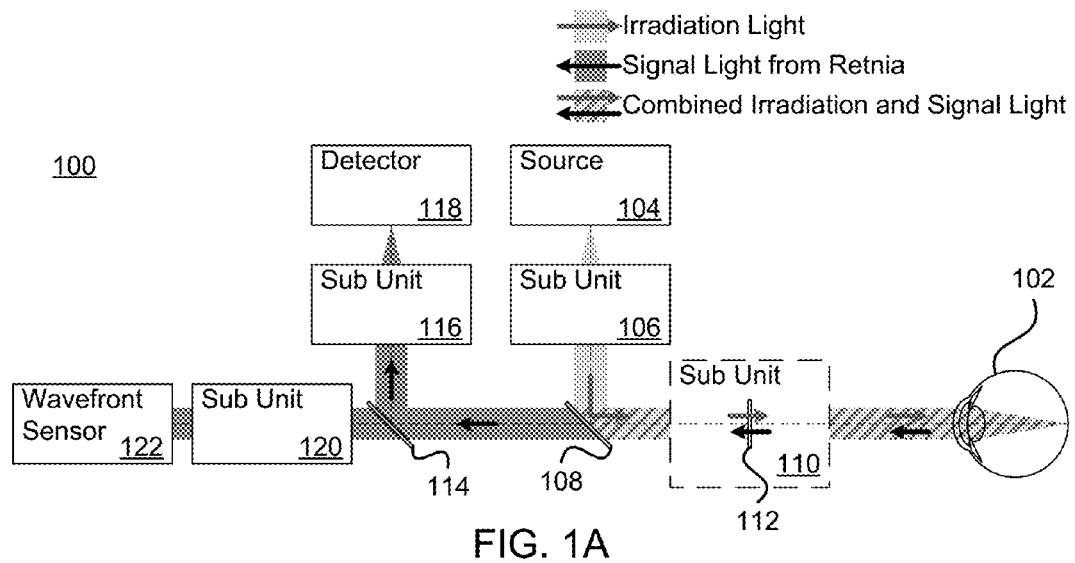
FIGS. 1A-C are illustrations of an AO-SLO.
Figure 1B:
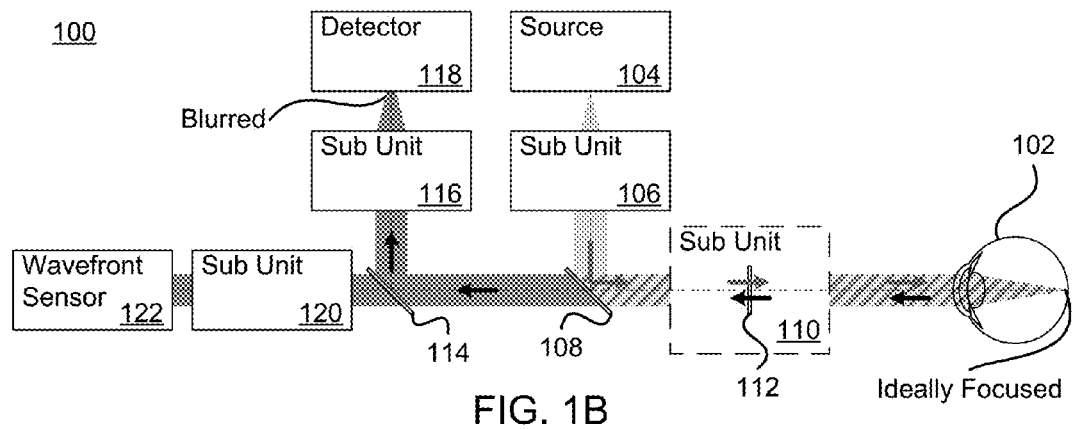
Figure 1C:
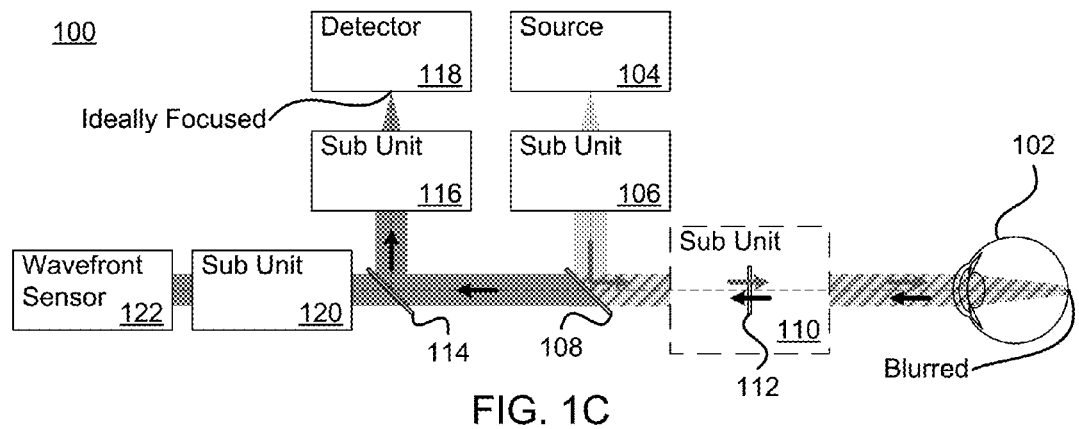

A problem with prior art systems is illustrated in FIGS. 1A-C. FIG. 1A is an illustration of an AO-SLO 100. An ophthalmoscope is a system or apparatus for obtaining information about an interior portion of the eye 102 (e.g., the fundus, object or subject, etc.). The AO-SLO 100 illustrated in FIG. 1A is a double path AO optical system that corrects both an irradiation light (light grey) to the eye 102 and image signal light (dark grey) from the retina of the eye 102 which propagate along a common optical path (dark and light grey stripes). Ideally, both wavefronts are corrected simultaneously, but in fact, when the irradiation light is ideally corrected and focused on the retina of the eye 102, the signal light from the retina may be corrected imperfectly. Because the optical path of the wavefront detection and of the image signal detection are different from that of the irradiation light. But the wavefront of the irradiation light and that of the signal light from the retina are corrected by a common wavefront corrector. Therefore, the signal light from the retina can't be ideally focused on a confocal pinhole in front of the image detector.

The AO-SLO scans a spot across the eye 102 from a light source 104 (or source) which produces the irradiation light that is scanned across the eye 102. The light source 104 sends the irradiation light to a first optical sub unit 106. The first optical sub unit 106 includes one or more optical components, which may include lenses, mirrors, apertures, and/or other optical components, all of which together may be used to shape the irradiation light which is then sent onto a first beamsplitter 108. The first beamsplitter 108 sends the irradiation light through a second optical sub unit 110.

The second optical sub unit 110 includes a first wavefront correction device 112. The first wavefront correction device 112 may be a spatial light phase modulator, a deformable mirror, an array of micromirrors, a deformable membrane, or some other device which can adjust and/or correct the wavefront of light. The second optical sub unit 110 may also include scanning optics, lenses, mirrors, apertures, and/or other optical components which are used to shape and scan the light across the eye 102. After passing through the second optical sub unit 110 the irradiation light is shined onto the eye 102.

Signal light from the retina is then collected by the second optical sub unit 110 which passes signal light back through the first wavefront correction device 112 and on through the first beamsplitter 108. The signal light which passes through the first beamsplitter 108 then hits a second beam splitter 114. A portion of the signal light which is incident on the second beam splitter 114 passes through a third optical sub unit 116 and is detected by a detector 118. The detector 118 includes a confocal pinhole. The third optical sub unit 116 includes lenses, mirrors, and/or other optical components which are used to focus the signal light onto the confocal pinhole. A portion of the signal light which is incident on the second beam splitter 114 passes through a fourth optical sub unit 120 and is detected by a wavefront sensor 122.

The information gathered by the wavefront sensor 122 is then used to control the first wavefront correction device 112. The first wavefront correction device 112 can thus be used to correct wavefront errors introduced by the subject eye 102. The first wavefront correction device 112 may also be used to correct for errors in the optical delivery and collection systems. The first wavefront correction device 112 may also be used to control the focal points. When the first wavefront correction device 112 is used to control the focal point includes an ideal focal point on the subject eye 102 and an ideal focal point on the confocal pinhole of the detector 118.

FIG. 1B is an illustration of when the first wavefront correction device 112 is used to focus the incident light onto the eye 102. Please note that as illustrated in FIG. 1B while the incident light is ideally focused onto the eye 102, the signal light as detected by the detector 118 is blurred. FIG. 1C is an illustration of when the first wavefront correction device 112 is used to focus the signal light onto on the confocal pinhole of the detector 118. Please note that as illustrated in FIG. 1C while the signal light as detected by the detector 118 is ideally focused, the incident light onto the eye 102 is blurred. Prior art methods of addressing this issue have included adjusting the position of the confocal pinhole, the detector 118, and/or adjusting the optics in the third optical sub unit 116.

Embodiment

Figure 2A:
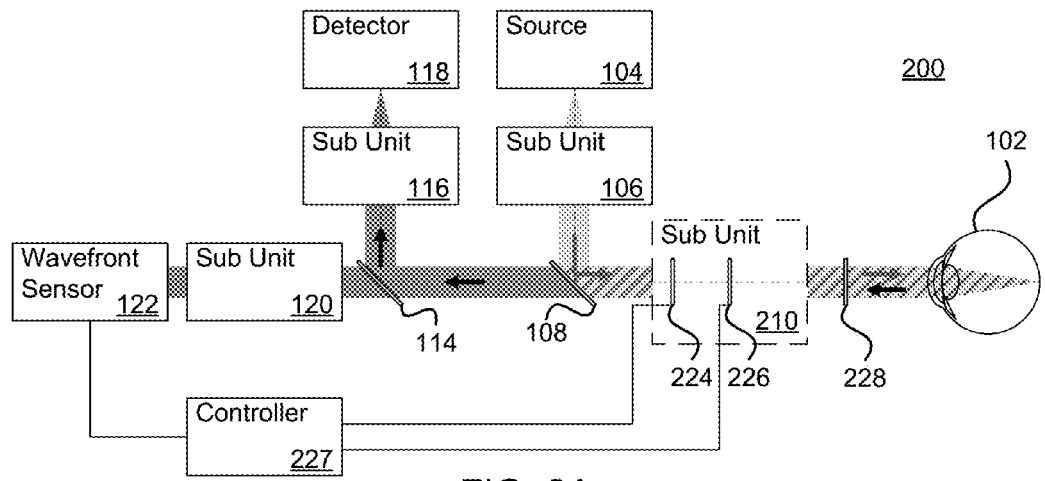
FIGS. 2A-E are illustrations of a system in which embodiments may be implemented.

FIG. 2A is an illustration an AO-SLO 200 that is an embodiment. The light source 104 sends the irradiation light to the first optical sub unit 106, which is then sent onto first beamsplitter 108. The first beamsplitter 108 sends the irradiation light through a fifth optical sub unit 210.

The fifth optical sub unit 210 includes a second wavefront correction device 224 and a third wavefront correction device 226 which are placed at optically conjugate positions to each other. The second wavefront correction device 224 modulates the wavefront of light with a first polarization, while not substantially modulating the wavefront of light with a second polarization. The second polarization is orthogonal to the first polarization. The third wavefront correction device 226 modulates the wavefront of light with the second polarization, while not substantially modulating the wavefront of light with the first polarization. The fifth optical sub unit 210 may also include scanning optics, lenses, mirrors, apertures, and/or other optical components which are used to shape and scan the light across the eye 102.

The ability of the wavefront correction devices 224 and 226 to not substantially modulate the wavefront of light with a specific polarization is dependent upon the device characteristics and alignment accuracy and the crosstalk performance requirements. The wavefront correction devices 224 and 226 may be a reflective type liquid crystal on silicon spatial light phase modulator (LCoS-SLM). In an alternative embodiment, the wavefront correction devices 224 and 226 are translucent type liquid crystal spatial light phase modulator (LC-SLM). In another alternative embodiment, the wavefront correction devices 224 and 226 are polarization sensitive modulators which when combined together or a combination of components which when combined together behave modulates the wavefront of light with a first polarization, while not substantially modulating the wavefront of light with a second polarization.

After passing through the second optical sub unit 210 the irradiation light is shined onto a polarization adjustment device 228 and then light is shined onto the eye 102. The polarization adjustment device may be a quarter wave plate.

Signal light from the eye then passes back through the polarization adjustment device 228 and is collected by the fifth optical sub unit 210 which passes signal light back through the third wavefront correction device 226, the second wavefront correction device 224, and on through the first beamsplitter 108. The signal light which passes through the first beamsplitter 108 then hits a second beam splitter 114. A portion of the signal light which is incident on the second beam splitter 114 passes through a third optical sub unit 116 and is detected by a detector 118. The detector 118 includes a confocal pinhole. The third optical sub unit 116 includes lenses, mirrors, and/or other optical components which are used to focus the signal light onto the confocal pinhole by correcting or altering aberrations in the wavefront at a conjugate pupil position that is along an optical path that includes the detector 118 after the second beam splitter 114. A portion of the signal light which is incident on the second beam splitter 114 passes through a fourth optical sub unit 120 and is detected by a wavefront sensor 122.

The information gathered by the wavefront sensor 122 is then used to control the second wavefront correction device 224 and the third wavefront correction device 226 via a controller 227. In an alternative embodiment, the fourth optical sub unit 120 includes a polarizer 454 and to detect only a single polarization component. The information gathered by the wavefront sensor 122 is then used to control the second wavefront correction device 224 and the third wavefront correction device 226.

Figure 2B:
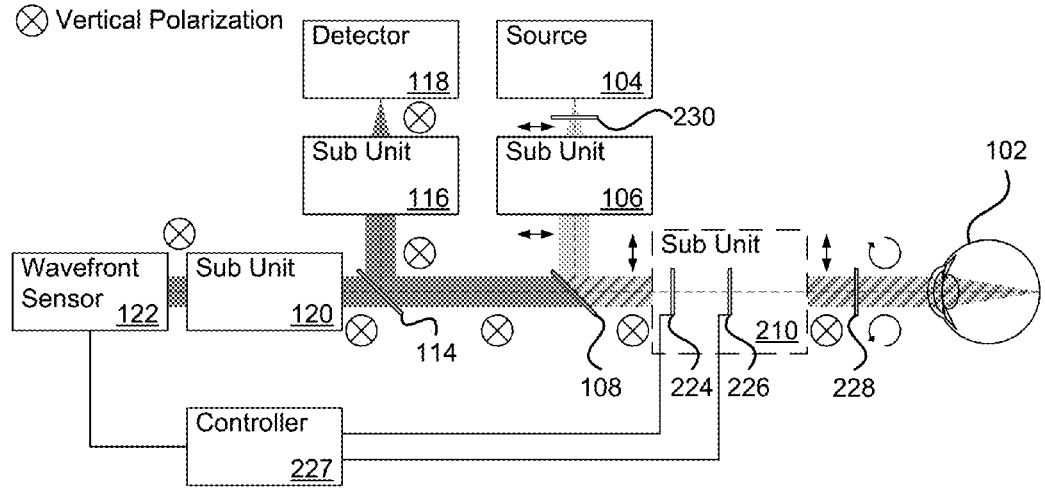

FIG. 2B is an illustration of the embodiment 200 in which the polarization of the light is indicated. The light source 104 sends the irradiation light through a polarizer 230. The polarizer 230 may be arranged to produce linearly polarized light (horizontal polarized). In an alternative embodiment, the source 104 is polarized. The polarized light is then sent through the first optical sub unit 106, which is then sent onto the first beamsplitter 108. The first beamsplitter 108 sends the irradiation light through a fifth optical sub unit 210. In an alternative embodiment, the first beamsplitter 108 is a polarization beam splitter (PBS) is used to both combine/split the light and polarize the and the embodiment 200 does not include polarizer 230, in which case horizontal polarized light from the source 104 is passed along while the vertical polarized light may be dumped. The PBS may be a cube type PBS or a plate type PBS.

Figure 2C:
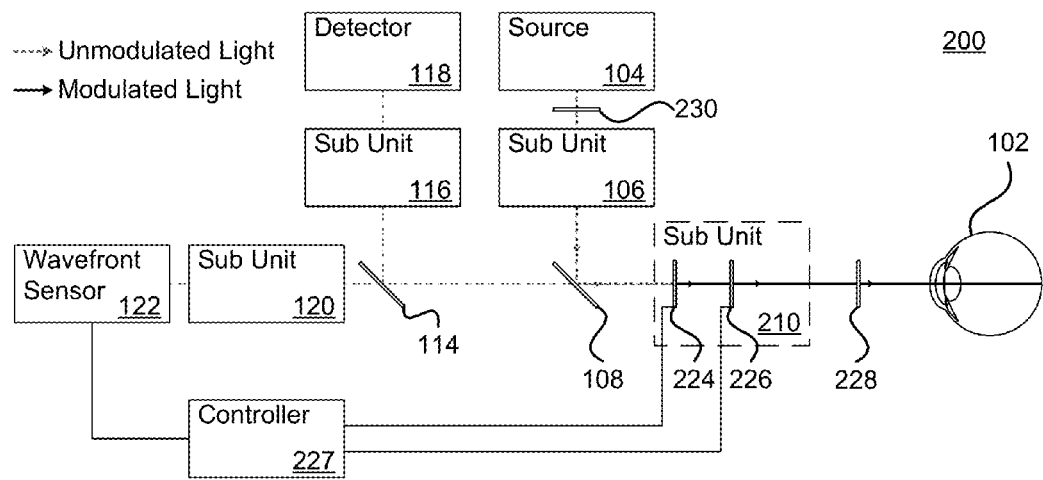
Figure 2D:
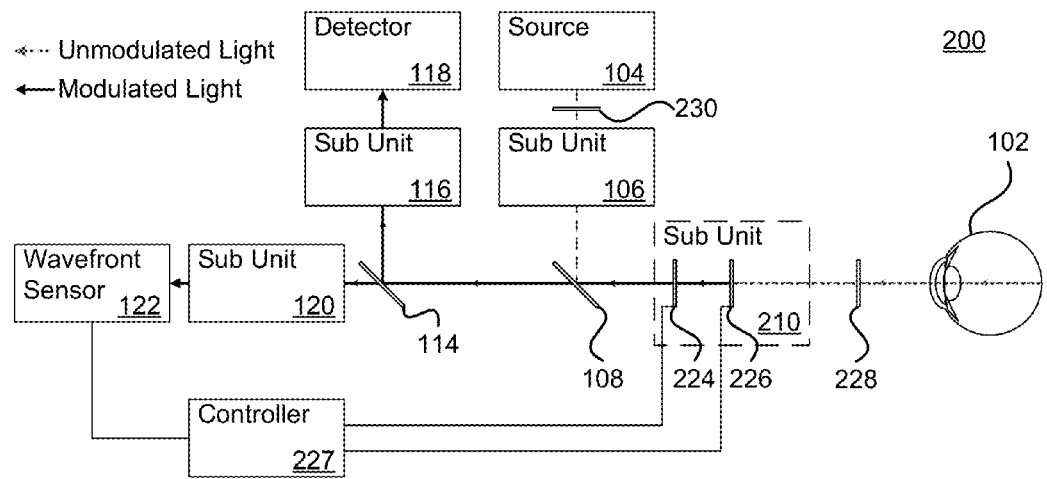

FIG. 2C is an illustration of the embodiment 200 in which the modulation of the irradiation light is indicated. FIG. 2D is an illustration of the embodiment 200 in which the modulation of the reflected light is indicated. The fifth optical sub unit 210 includes a second wavefront correction device 224 and a third wavefront correction device 226. The second wavefront correction device 224 modulates the wavefront of light with a horizontal polarization, while not substantially modulating the wavefront of light with a vertical polarization. The third wavefront correction device 226 modulates the wavefront of light with the vertical polarization, while not substantially modulating the wavefront of light with the horizontal polarization. Thus, the role of the second wavefront correction device 224 is to modulate only light from the source 104. The modulated horizontally polarized irradiation light will pass through the third wavefront correction device 226 substantially unaffected.

After passing through the second optical sub unit 210 the modulated horizontally polarized irradiation light is shined onto the polarization adjustment device 228 which may produce modulated clockwise "right hand" circular polarized irradiation light which is shined onto the eye 102. When the modulated clockwise circular polarized irradiation light is reflected by the eye 102 it will then be a counter clockwise "left hand" circular polarization signal light. The counter clockwise circular polarization signal light will then pass through the polarization adjustment device 228 to produce vertically polarized signal light.

The vertically polarized signal light from the eye 102 is collected by the fifth optical sub unit 210. The vertically polarized signal is then modulated by the third wavefront correction device 226 to produce modulated vertically polarized signal light. The modulated vertically polarized signal light will then pass through the second wavefront correction device 224 substantially unaffected, which is then goes through the first beamsplitter 108. The modulated vertically polarized signal light which passes through the first beamsplitter 108 then hits a second beam splitter 114. A portion of the modulated vertically polarized signal light which is incident on the second beam splitter 114 passes through a third optical sub unit 116 and is detected by a detector 118. A portion of the modulated vertically polarized signal light which is incident on the second beam splitter 114 passes through a fourth optical sub unit 120 and is detected by the wavefront sensor 122.

The information gathered by the wavefront sensor 122 is then used to control the second wavefront correction device 224 and the third wavefront correction device 226. Light which travels through the embodiment may be divided into these three optical paths. An illumination path A in which light travels from: the source 104 through the first optical sub unit 106; reflected by a first beamsplitter 108; through the second optical sub unit 210; and the polarization adjustment device 228. A wavefront detection path B in which light travels from the eye 102; through the polarization adjustment device 228 through the second optical sub unit 210; through the first beamsplitter 108; through the second beamsplitter 114; and through the fourth optical sub unit 120. An image detection path C in which light travels from the eye 102; through the polarization adjustment device 228 through the second optical sub unit 210; through the first beamsplitter 108; reflected by the second beam splitter 114; and through the third optical sub unit 116. Note that the aberrations for light reflected off the beamsplitters is different from light transmitted through the beamsplitters. A first wavefront correction matrix A (in the context of the present application bold uppercase letters are used to identify matrixes) is associated with the illumination path A. The first wavefront correction matrix A can be used to create a first control signal for the second wavefront correction device 224 as an offset. A second wavefront correction matrix B is associated with the wavefront detection path B and a third wavefront correction matrix C is associated with the image detection path C. The second wavefront correction matrix B and the third wavefront correction matrix C is used to create a second control signal for the third wavefront correction device 226 as an offset. The first control signal and the second control signal are optimized such that both wavefronts of the illumination light to the eye 102 and the return light from the eye 102 to the detector 118 are optimized independently.

Figure 2E:
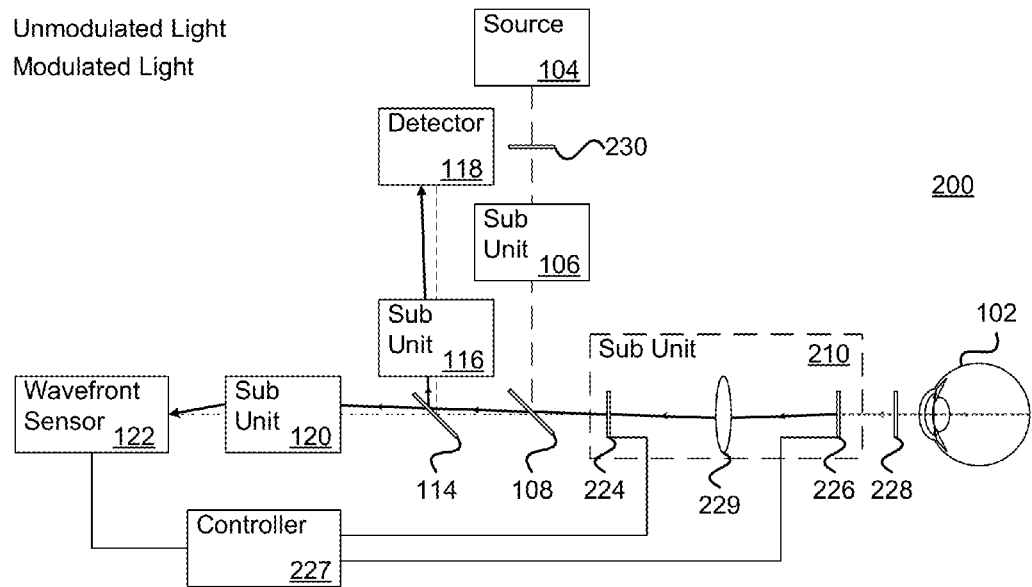

FIG. 2E is an illustration of signal light in an embodiment 200 used in a tilted imaging mode. A tilt signal is added only to the third wavefront correction device 226. Thus, the wavefront of the modulated vertically polarized signal light is tilted, which causes the direction of the light as it exits the third wavefront correction device 226 to be shifted. There are one or more optical components within the fifth optical sub unit 210 between the second wavefront correction device 224 and the third wavefront correction device 226, which are represented by a first optical component 229. The first optical component 229 may be implemented by one or more mirrors and/or lenses which may be configured so that second wavefront correction device 224 has a specific optical relationship with the third wavefront correction device 226 . . . . The tilted beam from the third wavefront correction device 226 may hit at the center of the second wavefront correction device 224 because both wavefront correction devices 224 and 226 are placed at positons that are optically conjugated to each other. The signal light is not tilted by the second wavefront correction device 224 and then travels to the wavefront sensor 122 and the image detector 118. The position of the beam at the wavefront sensor 122 also may not change because it is at an optically conjugate position with the wavefront correction devices 224 and 226. The wavefront sensor 122 does detect the tilt factor of the wavefront. The tilt factor which has been purposely added is ignored in the wavefront correction control method. The displacement amount of the beam spot at the image detector 118 may be controlled by changing the amount of the tilt factor in the control signal added to the third wavefront correction device 226. An advantage of this technique is that it allows the effect that in the prior art was obtained by a precision positioning of the confocal pinhole to be replaced with a change in signal provided to the wavefront correction device. This should improve the speed and reliability of the embodiment 200. Tilting the imaging field can be an effective means for the improving the resolution of an object that includes scattering objects which would otherwise prevent an image from being realized.

Dark field images can be obtained by intentionally shifting the position of the beam spot at a pinhole that is in front of the detector. In the prior art, the confocal pinhole is shifted mechanically in order to obtain these dark field images. This function can be accomplished without the accurate mechanical system by applying a tilt signal to the third wavefront correction device.

In an alternative embodiment, not only the tilt factor but other factors can be added to the modulation control signal which is provided to the third wavefront correction device 226 in order to get a desirable beam spot shape at the pinhole plane of the detector so that various kinds of information from the retina may be obtained. The illumination beam can also be modulated independently to illuminate the retina with desirable beam shape such as annular beam shape. The illumination beam may be a diffraction limited beam or non-diffraction limited beam.

Optical Sub Units

Figure 3A:
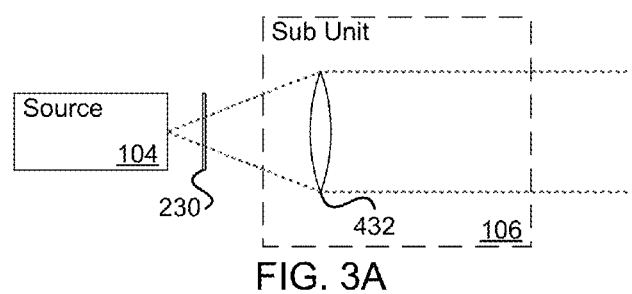
FIGS. 3A-D are illustrations of optical sub units which may be used in an embodiment.

FIGS. 3A-D are illustrations of the optical sub units used in FIGS. 2A-C. FIG. 3A is an illustration of the first optical sub unit 106. The first optical sub unit 106 receives illumination light from the source 104 and outputs collimated light. The first optical sub unit 106 may implemented with a first lens 432 after the polarizer 230. In an alternative embodiment, the polarizer may be placed within the first optical sub unit 106 or after the first optical sub unit 106. In another alternative embodiment, the source 104 may produce collimated light and the AO-SLO 200 may not include the first optical sub unit 106. The first optical sub unit 106 may include one or more optical components including: wavelength filters; spatial filters; lenses or mirrors. These one or more optical components may be use to reshape the illumination light or relay the illumination light. The first optical sub unit 106 may include one or more mirrors instead of the first lens 432.

Figure 3B:
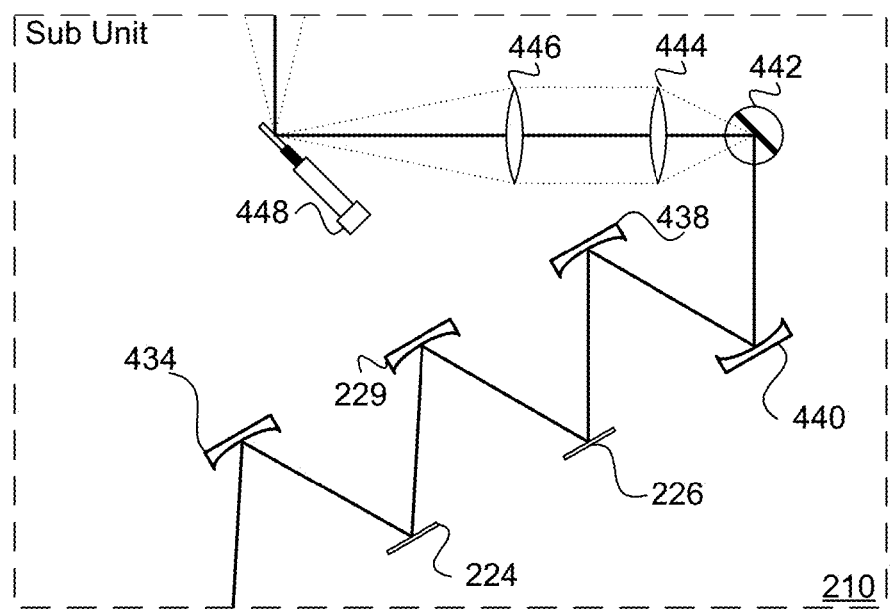

FIG. 3B is an illustration of the fifth optical sub unit 210. The fifth optical sub unit 210 receives illumination light from the first beamsplitter 108 and outputs the illumination light through the polarization adjustment device 228 and towards the subject 102 then gathers the light from the subject and returns it through the first beamsplitter 108. The illumination light from the first beamsplitter 108 may be reflected by a first curved mirror 434 onto the second wavefront correction device 224. The illumination light from the second wavefront correction device 224 may be reflected onto the first optical component 229 which may be a second curved mirror. The illumination light from the first optical component 229 may be reflected onto a third wavefront correction device 226. The illumination light from the third wavefront correction device 226 may be reflected onto a third curved mirror 438. The illumination light from the third curved mirror 438 may be reflected onto a fourth curved mirror 440. The illumination light from the fourth curved mirror 440 may be reflected onto a first scanner 442. The illumination light from the first scanner 442 may pass through a second lens 444 and a third lens 446 onto a second scanner 448. The illumination light from the second scanner 448 may then be reflected out of the fifth optical sub unit, through the polarization adjustment device 228 and towards the subject 102. The curved mirrors may be are arranged such second wavefront correction device 224 and the second wavefront correction device 228 are arranged in optical conjugate positions with each other. The first scanner 442 and the second scanner 448 may be arranged in optical conjugate positions with each other. The polarization adjustment device 228 may be placed within the fifth optical sub unit at some point between third wavefront correction device 226 and the subject 102. The relative positions of the second wavefront correction device 224 and the third wavefront correction device 226 may be swapped.

Return light from the subject 102 passes back through the fifth optical sub unit 210 along substantially the same path as the illumination light. In this instance, substantially refers to within the optical alignment tolerances of the system taking into account any purposeful deviation such as a tilt signal which is done to obtain specific imaging results.

Figure 3C:
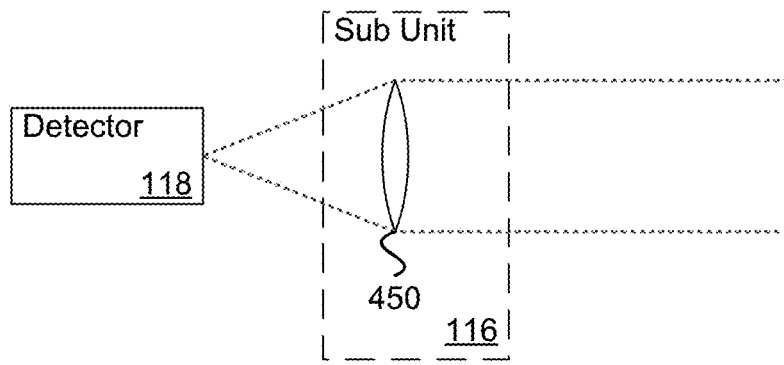

FIG. 3C is an illustration of the third optical sub unit 116. The third optical sub unit 116 receives the return light from the second beamsplitter 114 and sends the return light to the detector 118. The detector 118 may be confocal imaging detector and may include one or more pinholes in front of the detector 118. The third optical sub unit may include a fourth lens 450 for focusing the return light onto the detector 118 or the one or more pinholes that might be in front of the detector 118. The fourth lens 450 may be replaced with an equivalent curved mirror. The third optical sub unit may include additional optical wavelength filter, spatial filters, mirrors, or lenses which shape the return light so as to alter the performance of what is detected.

Figure 3D:
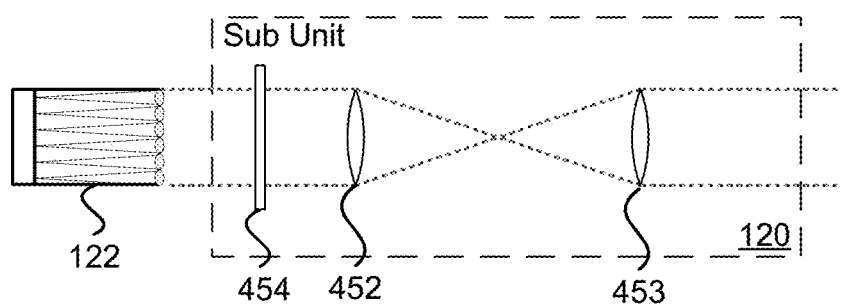

FIG. 3D is an illustration of the fourth optical sub unit 120. The fourth optical sub unit 120 receives the return light from the second beamsplitter 114 and sends the return light to the wavefront sensor 122. The fourth optical sub unit 120 may include a fifth lens 452 and a sixth lens 453 which images the return light onto the wavefront sensor 122. The fourth optical sub unit 120 may also include the polarizer 454.

Calibration Measurements

Figure 4A:
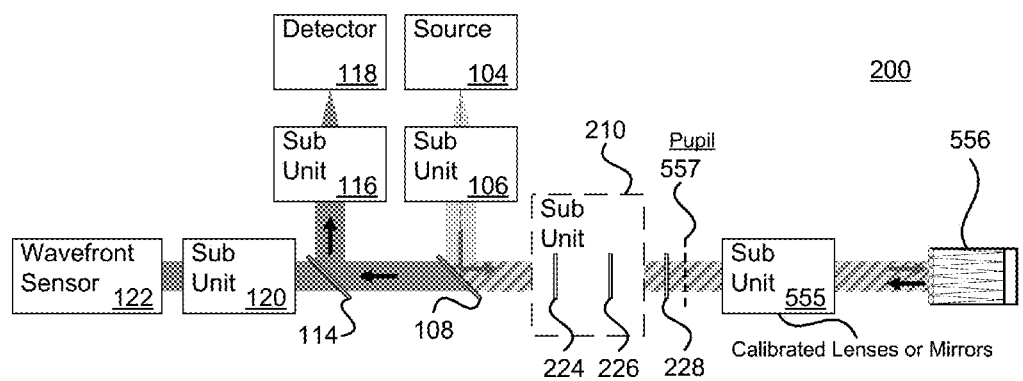
FIGS. 4A-D are illustrations of an embodiment that is modified to obtain calibration measurements.

FIGS. 4A-D is an illustration of how the AO-SLO may be modified so that the calibration measurements may be obtained. The first wavefront correction matrix A (in the context of the present application bold uppercase letters are used to identify matrixes) may be calculated based upon the optical components along the illumination path A. Alternatively, the first wavefront correction matrix A may be calculated based upon a first calibration measurement of the wavefront by a second wavefront sensor 556 which may be placed after the polarizer in order to measure the illumination light that is incident upon the eye as illustrated in FIG. 4A. A sixth optical sub unit 555 may be positioned between the polarization adjustment device 228 and the second wavefront sensor 556. The sixth optical sub unit 555 is a calibrated optical component with known optical properties. The sixth optical sub unit 555 may include one or more mirrors and/or lenses. The sixth optical sub unit 555 may be used such that the full area of second wavefront sensor 556 is used. The wavefront sensor 556 is placed at the pupil conjugate position. The pupil conjugate position is a position that is optically conjugate to a pupil 557. The pupil 557 is located after the polarization adjustment device 228. The pupil 557 may be located at the iris of a subject 102 if the subject was being imaged. The effect of the sixth optical sub unit 555 may be removed in order to come upon with the first wavefront correction matrix A. A model crystalline lens 559 may also be placed between the polarization adjustment device 228 and the second wavefront sensor 556 so that the effect of a model eye may be approximated and compensated for. The model crystalline lens 559 may have the optical properties of a typical eye or an atypical eye. The first wavefront correction matrix A may be used to control the second wavefront correction device 224 and the effect measured by the second wavefront sensor 556 which is then fed back to the second wavefront correction device 224 until an optimum imaging spot is obtained or a specific type (e.g. annular) of imaging spot is obtained. The first wavefront correction matrix A may be measured and/or calculated under multiple imaging conditions including: temperature, scanning area, scanning position, distance from the polarization device 228, distance from the model crystalline lens 559, different model crystalline lenses, etc. In an alternative embodiment, instead of using the second wavefront sensor 556, the wavefront sensor 122 is moved temporarily from after the fourth optical sub unit 120 to after the polarization adjustment device 228.

Figure 4B:
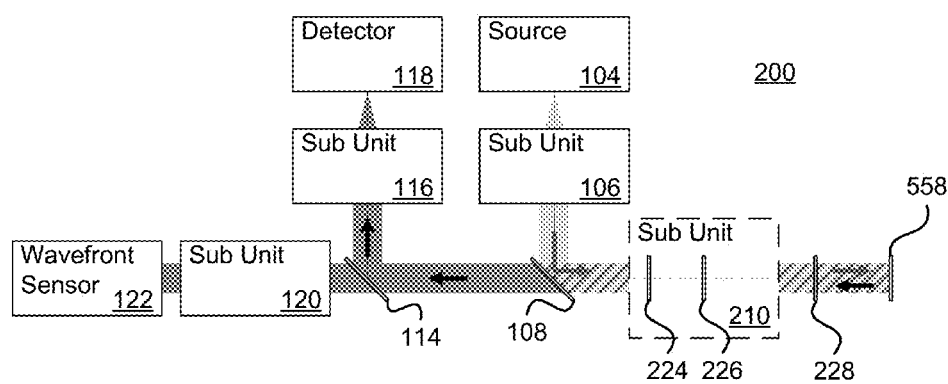
Figure 4C:
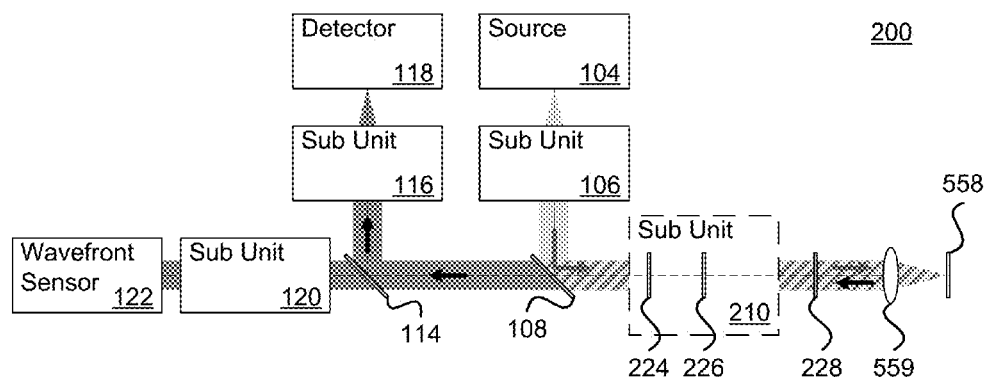

The second wavefront correction matrix B may be calculated based upon the optical components along the wavefront detection path B. Alternatively, the second wavefront correction matrix B may be calculated based upon a second calibration measurement by the wavefront sensor 122 in which the object 102 has been replaced with a reflective surface 558 as illustrated in FIG. 4B which is located at the pupil 557 or at a position that is optically conjugate to the pupil 557. The reflective surface 558 may be a flat mirror. A model crystalline lens 559 may also be placed at the pupil 557 and the reflective surface 558 may be placed at the focal plane of the model crystalline lens 559. In this case, the reflective surface 558 may be a piece of paper, a calibrated reference reflector with a dispersive surface so that the effect of a model eye may be approximated and compensated for as illustrated in FIG. 4C. The second calibration measurement may be made while the first wavefront correction matrix A is used to control the second wavefront correction device 224. The second wavefront correction matrix B may be measured and/or calculated under multiple imaging conditions including: temperature, scanning area, scanning position, distance from the polarization device 228, distance from the model crystalline lens 559, different model crystalline lenses, etc. The dispersive reflective surface 558 (and the model crystalline lens 559) may be used to measure the aberration of the "one-way" wavefront detection path B without the influence of the illumination path A. A small beam spot focused on the dispersive reflective surface 558 by the model crystalline lens 559 may be considered "a second light source" and the diffused light from the spot will not include the wavefront information of the illumination light. Therefore, the aberration information relative to both wavefront detection path B and image detection path C are detected independently by measuring the diffused light from the spot. A piece of paper or dispersive panel may be used as "a dummy retina".

Figure 4D:
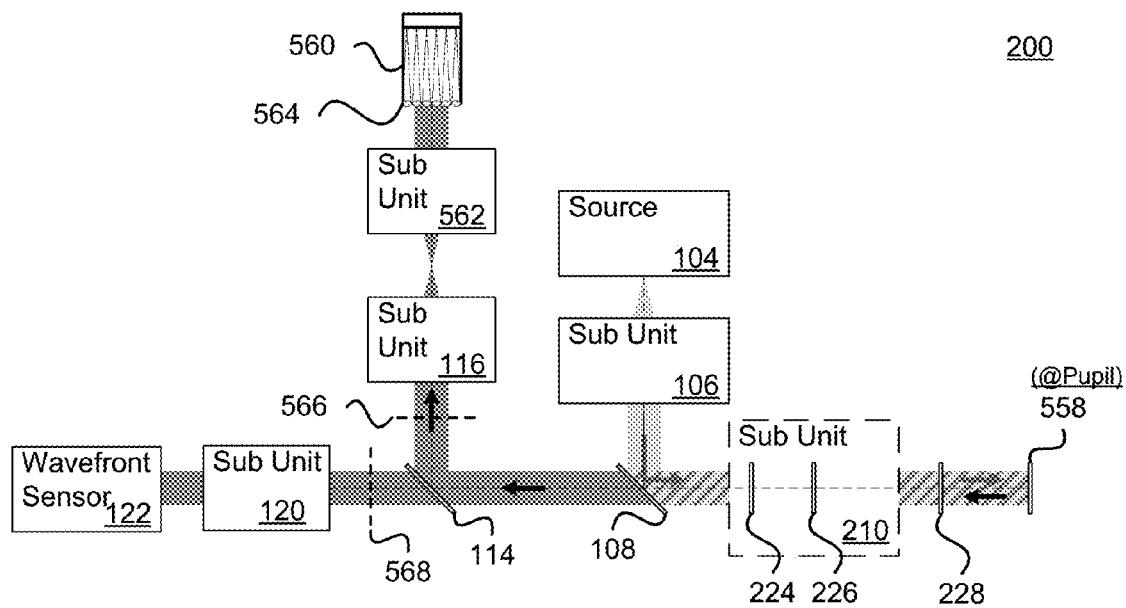

The third wavefront correction matrix C may be calculated based upon the optical components along the image detection path C. Alternatively, the third wavefront correction matrix C may be calculated based upon a third calibration measurement by a third wavefront sensor 560 that may be temporarily placed in the area of the detector 118 and in which the object 102 has been temporarily replaced with the reflective surface 558 as illustrated in FIG. 4D. A seventh optical sub unit 562 may be positioned between the fifth optical sub unit 116 and the third wavefront sensor 560 such that a full area of third wavefront sensor 560. The wavefront sensor 560 is may be placed at a pupil conjugate position 564. The seventh optical sub unit 562 may include one or more mirrors or lenses which specific optical properties which can be accounted for in the calibration step. The third calibration measurement may be made at the same time as the second calibration measurement. A model crystalline lens 559 may also be placed between the polarization adjustment device 228 and the reflective surface 558 so that the effect of a model eye may be approximated and compensated for. The third calibration measurement may be made while the first wavefront correction matrix A is used to control the second wavefront correction device 224. The third wavefront correction matrix C may be measured and/or calculated under multiple imaging conditions including: temperature, scanning area, scanning position, distance from the polarization device 228, distance from the model crystalline lens 559, different model crystalline lenses, etc. The dispersive reflective surface 558 (and the model crystalline lens 559) may be used to measure the aberration of "one-way" wavefront detection path B without the influence of the illumination path A. In an alternative embodiment, instead of using the third wavefront sensor 560, the wavefront sensor 122 is moved temporarily from after the fourth optical sub unit 120 to the location in the area of the detector 118. In an alternative embodiment, instead of using the third wavefront sensor 560, the second wavefront sensor 556 is moved temporarily to the location of the detector. The third wavefront correction matrix C may be used to control the third wavefront correction device 226 and the effect measured by the third wavefront sensor 560 which is then fed back to the third wavefront correction device 226 until an optimum detection spot is obtained or a specific type of detection spot is obtained. Additional pupil conjugate positions 566 and 568 are shown in FIG. 4D. The third wavefront sensor 560 may be placed at these pupil conjugate positions.

Specific tilt functions may be added to the third wavefront correction device 226, the effect of these tilt functions may be calculated or measured by the third wavefront sensor 560. In most embodiments, there should be a linear relationship between the third wavefront correction matrix C and the second wavefront correction matrix B. The relationship between the third wavefront correction matrix C and the second wavefront correction matrix B may be measured under a variety of imaging conditions including: temperature, scanning area, scanning position, distance from the polarization device 228, distance from the model crystalline lens 559, different model crystalline lenses, tilt functions, etc.

Figure 5:
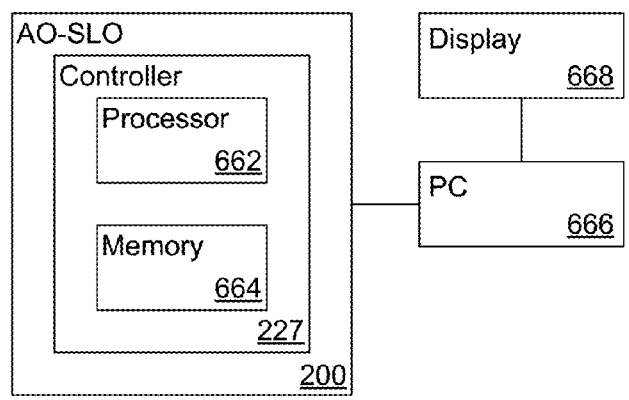
FIG. 5 is an illustration of controller used in an embodiment.

FIG. 5 is an illustration of the controller 227 that may be used in an embodiment. The controller 227 receives input signals and outputs control signals. The controller 227 may be a general purpose computer, a device specifically designed to controller the AO_SLO 200, or hybrid device that uses some custom electronics along with a general purpose computer. The input signals and control signals maybe digital signals or analog signals. The controller 227 may include an analog to digital converter (ADC) and a digital to analog converter (DAC). The input signals may include one more signals such as a signal from the wavefront sensor 122, a signal from the detector, and one or more signals from one or more other sensors. The control signals may include the first control signal to the second wavefront correction device 224 and a second control signal to the third wavefront correction device 226. The control signals may include additional signals to the scanners, and light sources of the AO-SLO.

The controller 227 includes a processor 662. The processor may be a microprocessor, a CPU, an ASIC, a DSP, or a FPGA. The controller 227 may include a memory 664. The memory 664 may store calibration information such as the first wavefront correction matrix A; the second wavefront correction matrix B, and the third wavefront correction matrix C. The memory 664 may also store software for controlling the AO-SLO 200. The memory 664 may be a form of non-transitory computer readable storage medium. The storage non-transitory computer readable medium may include, for example, one or more of a hard disk, a random-access memory (RAM), a read only memory (ROM), a distributed storage system, an optical disk (CD, DVD or Blu-Ray Disc, a flash memory device, a memory card, or the like.

The controller 227 may be connected to a computer 666 via a direction connection, a bus, or via a network. The computer 666 may include input devices such as a keyboard, a mouse or a touch screen. The controller may include input device such as a keyboard, a mouse or a touch screen, knobs, switches, and/or buttons. The computer 666 may be connected to a display 668. The results of the AO-SLO may be presented to a user via the display 668.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An adaptive optical imaging system for imaging an object comprising:
   a light source that produces irradiation light to irradiate the object;
   a first modulator that is a polarization sensitive spatial light phase modulator, so as to modulate the irradiation light with a first polarization produced by the light source and does not substantially modulate light with a second polarization that is orthogonal to the first polarization;
   a polarization adjustment device that converts the polarization of light that has passed through the first modulator before it irradiates the object and converts the polarization of reflected light from the object that has been irradiated with the irradiation light, such that the reflected light has a second polarization that is orthogonal to the first polarization;
   a wavefront sensor that measures a wavefront of the reflected light;
   an image signal detector;
   a second modulator that is a polarization sensitive spatial light phase modulator, placed between the image signal detector and the polarization adjustment device so as to not modulate the irradiation light and modulate the reflected light; and
   a controller that sends:
   first instructions to the first modulator to correct the aberration of the irradiation light on the object, and
   second instructions to the second modulator to correct the aberration of the reflected light on the image signal detector.

2. The adaptive optical imaging system of claim 1, further comprising a polarizer that turns irradiation light produced by the light source into polarized irradiation light.

3. The adaptive optical imaging system of claim 2, wherein the polarized irradiation light is linearly polarized irradiation light.

4. The adaptive optical imaging system of claim 1, wherein the polarization adjustment device is a quarter wave plate.

5. The adaptive optical imaging system of claim 1, wherein the object is an eye.

6. The adaptive optical imaging system of claim 1, wherein the first modulator is a liquid crystal phase modulator.

7. The adaptive optical imaging system of claim 1, wherein the image signal detector is a confocal imaging detector that includes a pinhole; and the controller sends second instructions to the second modulator that corrects the aberration of the reflected light on the pinhole of the confocal imaging detector.

8. The adaptive optical imaging system of claim 1, further comprising a polarization beam splitter, wherein the polarization beam splitter is arranged to:

receive the irradiation light from a first direction;

output the irradiation light with the first polarization in a second direction from the polarization beam splitter;

receive the reflected light with the second polarization that has been modulated by the second modulator from a third direction that is substantially parallel to the second but in the opposite direction; and output the reflected light with the second polarization that has been modulated by the second modulator in a fourth direction that is different from the first direction.

9. The adaptive optical imaging system of claim 1, a tilt signal is added to the second modulator such that a position at which the reflected light is focused on the detector is shifted.

10. The adaptive optical imaging system of claim 9, wherein the image signal detector is a confocal imaging detector that includes a pinhole; and the reflected which has been shifted by the tilt function is shifted relative to the pinhole.

11. The adaptive optical imaging system of claim 1, wherein the first instructions that the controller sends to the first modulator takes into account first calibration information which represents first distortions of a first wavefront that is used to irradiate the object.

12. The adaptive optical imaging system of claim 11, wherein the first distortions include distortions caused by optical components between the object and the light source of the irradiation light.

13. The adaptive optical imaging system of claim 12, wherein the first distortions also include distortions caused by the source of the irradiation light.

14. The adaptive optical imaging system of claim 1, wherein the second instructions that the controller sends to the second modulator takes into account second calibration information which represents second distortions of a second wavefront of reflected light that is incident on the image signal detector.

15. The adaptive optical imaging system of claim 14, wherein the second distortions include distortions caused by optical components between the object and the image signal detector.

16. The adaptive optical imaging system of claim 15, wherein the second distortions include distortions caused by optical components between the object and the wavefront sensor.

17. The adaptive optical imaging system of claim 1, wherein the first instructions are used to adjust the shape of the irradiation light on the object.

18. The adaptive optical imaging system of claim 1, wherein the first instructions are used to adjust the shape of the reflected light on the image signal detector.

19. The adaptive optical imaging system of claim 1, wherein the object is a fundus of an eye.

20. The adaptive optical imaging system of claim 1, wherein the irradiation light and the reflected light both pass through the first modulator, the second modulator, and the polarization adjustment device.

21. The adaptive optical imaging system of claim 1, wherein the first modulator modulates the irradiation light with the first polarization by using a first wavefront correction value, and wherein the second modulator modulates the reflected light with the second polarization by using a second wavefront correction value different from the first wavefront correction value.

* * * * *